United States Patent [19]

Large

[11] 4,451,463
[45] May 29, 1984

[54] ALCOHOL DERIVATIVES

[75] Inventor: Michael S. Large, Congleton, England

[73] Assignee: Imperial Chemical Industries PLC, London, England

[21] Appl. No.: 353,416

[22] Filed: Mar. 1, 1982

[30] Foreign Application Priority Data

Mar. 24, 1981 [GB] United Kingdom ............... 8109217

[51] Int. Cl.³ ............... C07D 239/42; C07D 239/34; A61K 31/51
[52] U.S. Cl. ............... 424/249; 424/251; 424/263; 424/269; 424/270; 424/272; 424/273 R; 424/273 P; 544/194; 544/204; 544/317; 544/335; 544/336; 544/408; 546/297; 546/308; 548/128; 548/130; 548/132; 548/133; 548/184; 548/193; 548/230; 548/235; 548/255; 548/265; 548/266; 548/301; 548/362
[58] Field of Search ............... 544/317, 335, 408, 336, 544/204, 194; 546/297, 306; 424/249, 251, 263

[56] References Cited

U.S. PATENT DOCUMENTS

| | | | |
|---|---|---|---|
| 4,242,350 | 12/1980 | Yellin et al. | 424/270 |
| 4,242,351 | 12/1980 | Yellin et al. | 424/270 |
| 4,244,966 | 1/1981 | Lippmann et al. | 424/270 |
| 4,267,189 | 5/1981 | Lippmann et al. | 424/270 |
| 4,315,009 | 2/1982 | Jones et al. | 424/270 |
| 4,342,765 | 8/1982 | Jones et al. | 424/270 |
| 4,362,728 | 12/1982 | Yellin | 424/249 |

Primary Examiner—Robert Gerstl
Attorney, Agent, or Firm—Cushman, Darby & Cushman

[57] ABSTRACT

This invention relates to alcohol derivatives which are histamine H-2 antagonists and which inhibit gastric acid secretion. According to the invention there is provided a guanidine derivative of the formula I:

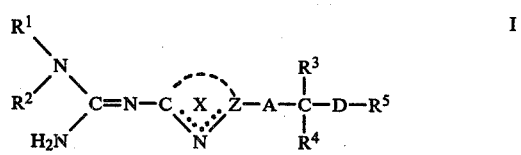

in which $R^1$ and $R^2$, same or different, are hydrogen or 1-10C alkyl, 3-8C cycloalkyl or 4-14C cycloalkylalkyl, each alkyl, cycloalkyl or cycloalkylalkyl optionally carrying one or more F, Cl or Br atoms, provided that one of $R^1$ and $R^2$ is halogen-substituted, or $R^2$ is hydrogen and $R^1$ is $R^5$—E—W— in which W is 2-6C alkylene optionally substituted by 1 or 2 1-4C alkyl, E is O, S, SO, $SO_2$ or $NR^6$ in which $R^6$ is H or 1-6C alkyl, $R^5$ is H or 1-6C alkyl optionally substituted by 1 or 2 1-4C alkyls, or $R^5$ and $R^6$ are joined to form a pyrrolidine, piperidine, morpholine, piperazine or N-methylpiperazine ring, or $R^2$ is hydrogen and $R^1$ is hydrogen or 1-10C alkyl, 3-8C cycloalkyl, 4-14C cycloalkylalkyl, 3-6C alkenyl, 3-6C alkynyl, 1-6C alkanoyl, 6-10C aryl, 7-11C arylalkyl or 7-11C aroyl, the aryl, arylalkyl and aroyl radicals being optionally substituted, ring X is a heterocyclic ring as defined in the specification; A is phenylene or 5-7C cycloalkylene or a 1-8C alkylene into which is optionally inserted one or two groups; D is oxygen or sulphur; $R^3$, $R^4$ and $R^5$ are hydrogen or a variety of radicals described in the specification: and the pharmaceutically-acceptable acid-addition salts thereof. Manufacturing processes and pharmaceutical compositions are also described.

10 Claims, No Drawings

ALCOHOL DERIVATIVES

This invention relates to alcohol derivatives which are histamine H-2 antagonists and which inhibit gasteric acid secretion.

It is postulated that the physiologically-active compound histamine, which occurs naturally within the animal body, is able to combine, in the course of exerting its activity, with certain specific receptors of which there are at least two distinct and separate types. The first has been named the H-1 receptor (Ash and Schild, *Brit. J. Pharmac.* 1966, 27, 427) and the action of histamine at this receptor is blocked (antagonised) by classical "antihistamine" drugs such as mepyramine. The second histamine receptor has been named the H-2 receptor (Black et al., *Nature*, 1972, 236, 385) and the action of histamine at this receptor is blocked by drugs such as cimetidine. It is known that one of the results of the blockade of the action of histamine at the H-2 receptor is the inhibition of the secretion of gastric acid and a compound which possesses this ability is therefore useful in the treatment of peptic ulcers and other conditions caused or exacerbated by gastric acidity.

In U.K. Patent Application No. 2001624 and European Patent Publications Nos. 6286, 6679, 30092 and 45155 there are described histamine H-2 receptor antagonists which are guanidino heterocycles carrying a side chain to the end of which is attached a modified guanidine residue. It has now been discovered that if this modified guanidine is replaced by a hydroxy radical there are obtained potent histamine H-2 receptor antagonists.

According to the invention there is provided a guanidine derivative of the formula I:

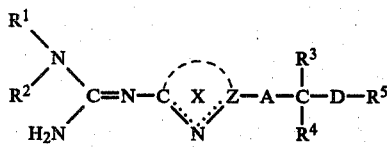

in which $R^1$ and $R^2$, which may be the same or different, are hydrogen atoms or branched or unbranched 1-10C alkyl, 3-8C cycloalkyl or 4-14C cycloalkylalkyl radicals, each alkyl, cycloalkyl or cycloalkylalkyl radical being optionally substituted by one or more halogen atoms selected from fluorine, chlorine and bromine atoms, provided that at least one of $R^1$ and $R^2$ is a halogen-substituted alkyl, cycloalkyl or cycloalkylalkyl radical, and provided that there is no halogen substituent on the carbon atom of the alkyl, cycloalkyl or cycloalkylalkyl radical which is directly attached to the nitrogen atom, or $R^2$ is a hydrogen atom and —$R^1$ is a radical of the formula II:

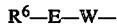 $R^6$—E—W—         II in which W is an unbranched 2-6C alkylene chain which is optionally substituted by one or two 1-4C alkyl radicals, E is an oxygen or sulphur atom, a sulphinyl or sulphonyl radical, or a radical of the formula $NR^7$ in which $R^7$ is a hydrogen atom or a 1-6C alkyl radical, $R^6$ is a hydrogen atom or an unbranched 1-6C alkyl radical which is optionally substituted by one or two 1-4C alkyl radicals, or $R^6$ and $R^7$ are joined to form, together with the nitrogen atom to which they are attached, a pyrrolidine, piperidine, morpholine, piperazine or n-methylpiperazine ring, or $R^2$ is a hydrogen atom and $R^1$ is a hydrogen atom or a 1-10C alkyl, 3-8C cycloalkyl, 4-14C cycloalkylalkyl, 3-6C alkenyl, 3-6C alkynyl, 1-6C alkanoyl, 6-10C aryl, 7-11C arylalkyl or 7-11C aroyl radical, the aryl, arylalkyl and aroyl radicals being optionally substituted on the aryl ring by one or two substituents selected from fluorine, chlorine and bromine atoms and 1-6C alkyl, 1-6C alkoxy, 1-6C alkylthio, trifluoromethyl, hydroxy and amino radicals; in ring X the dotted line is a double bond on one side of the nitrogen atom and Z is a carbon or nitrogen atom such that ring X is a 5- or 6-membered aromatic heterocyclic ring which contains at least one nitrogen atom and may optionally contain one or two additional hetero atoms selected from oxygen, nitrogen and sulphur atoms, which heterocyclic ring may, where possible, carry one or two optional substituents, the optional substituents or ring X being selected from fluorine, chlorine and bromine atoms and 1-6C alkyl, 1-6C alkoxy, 1-6C alkylthio, trifluoromethyl, hydroxy and amino radicals; A is a 1-8C alkylene chain which is optionally substituted by one or two 1-3C alkyl radicals and into which is optionally inserted, as part of the backbone of the chain, an NH or a 1-6C N-alkyl radical or one or two groups selected from oxygen and sulphur atoms and cis and trans vinylene, ethynylene, phenylene and 5-7C alkylene radicals, provided that no two insertions selected from oxygen and sulphur atoms and NH and N-alkyl radicals are directly attached one to the other and provided that when the optional insertion is NH or N-alkyl, that insertion is directly attached to ring X, or A is a 5-7C cycloalkylene radical or, when Z is a nitrogen atom, A is a phenylene radical; $R^3$ is a hydrogen atom or a 1-6C alkyl, 3-8C cycloalkyl, 4-12C cycloalkylalkyl, 3-6C alkenyl, 3-6C alkynyl or 2-8C alkoxyalkyl radical; $R^4$ is a hydrogen atom or a 1-6C alkyl radical; or A-$CR^3R^4$ is an oxy-1,4-cyclohexylene radical; D is an oxygen or sulphur atom; $R^5$ is a hydrogen atom or a 1-6C alkyl, 1-6C alkanoyl, 6-10C aryl, 7-11C arylalkyl or 7-11C aroyl radical, the aryl, arylalkyl and aroyl radicals each being optionally substituted by one or two substitutents selected from fluorine, chlorine and bromine atoms and 1-6C alkyl, 1-6C alkoxy, 1-6C alkylthio, cyano, trifluoromethyl, hydroxy and amino radicals: and the pharmaceutically-acceptable acid-addition salts thereof.

It is to be understood that, in the above formula I and throughout this specification, although the double bond in the guanidine residue attached to ring X has been inserted in a particular position, other tautomeric forms are possible, and this invention includes such tautomeric forms within its scope, both in terms of the compounds of the invention and in terms of the manufacturing processes. It is also to be understood that when A is or contains a cycloalkylene radical the groups attached to this radical may be in the cis or trans configuration. When A is or contains a cycloalkylene radical and/or when A is an alkylene chain substituted by one or two alkyl radicals and/or when $R^3$ and $R^4$ are different, the compound of the formula I will, in most instances, contain at least one asymmetric centre. In such cases the compound of the formula I will therefore exist in at least two enantiomeric forms, the precise number being determined by the number of asymmetric centres. The biological activity, as hereinafter defined, of these enantiomeric forms may differ, and it is therefore to be understood that this invention encompasses the racemate of the formula I, including any possible diastereoisomeric forms, and any enantiomeric form which possesses the disclosed biological activity, it being a matter of common general knowledge to one skilled in the art how to separate diastereoisomeric forms and how to separate a racemate into its enantiomers and determine the biological activity of each.

A particular value for $R^1$ or $R^2$ when it is a halogen-substituted alkyl radical is a 2,2,2-trifluoroethyl, 2,2,2-trichloroethyl, 2-chloro-2,2-difluoroethyl, 2,2-dichloro-2-fluoroethyl, 2-bromo-2,2-difluoroethyl, 2,2-dibromo-2-fluoroethyl, 2-fluoroethyl, 2-chloroethyl, 2,2-difluoroethyl, 2,2-dichloroethyl, 2-chloro-2-fluoroethyl, 2-bromo-2-fluoroethyl, 2,2,3,3-tetrafluoropropyl, 2,2,3,3,3-pentafluoropropyl, 1,1,1,3,3,3-hexafluoroisopropyl, 1,3-dichloro-1,1,3,3-tetrafluoroisopropyl, 1-chloro-1,1,3,3,3-pentafluoroisopropyl, 1,3-difluoroisopropyl or 2,2,3,3,4,4-heptafluorobutyl radical.

A particular value for $R^1$ or $R^2$ when it is a halogen-substituted cycloalkyl radical is a 2,2,3,3-tetrafluorocyclopropyl, 2-chloro-2,3,3-trifluorocyclopropyl, 2,2-difluorocyclopropyl, 2-chloro-3,3-difluorocyclopropyl, 2,2,3,3,4,4-hexafluorocyclobutyl or 2-chloro-2,3,3,4,4-pentafluorocyclobutyl radical.

A particular value for $R^1$ or $R^2$ when it is a halogen-substituted cycloalkylalkyl radical is a (1,2,2,3,3-pentafluorocyclopropyl)metnyl, (2-chloro-1,2,3,3-tetrafluorocyclopropyl)methyl, (1,2,2,3,3,4,4-heptafluorocyclobutyl)metnyl or (2-chloro-1,2,3,3,4,4-hexafluorocyclobutyl)methyl radical.

A particular value for $R^1$ and $R^2$ when it is an alkyl radical is a methyl, ethyl, propyl, isopropyl or butyl radical.

A particular value for $R^1$ or $R^2$ when it is a cycloalkyl radical is a cyclopropyl or cyclobutyl radical.

A particular value for $R^1$ or $R^2$ when it is a cycloalkylalkyl radical is a cyclopropylmethyl or cyclobutylmethyl radical.

A particular value for the optional substituent on w is a methyl radical. A particular value for $R^5$ is a hydrogen atom or a methyl radical.

A particular value for $R^6$ is a hydrogen atom or a methyl radical.

A particular value for the radical of the formula II is a 2-methoxyethyl, 2-hydroxyethyl, 5-hydroxypentyl, 2-methylthioethyl or 2-dimethylaminoethyl radical.

When $R^2$ is a hydrogen atom a particular value for $R^1$ is a hydrogen atom or a methyl, ethyl, propyl, isopropyl, butyl, cyclohexyl, cyclohexylmethyl, allyl, propargyl, acetyl, phenyl, benzyl or benzoyl radical, the phenyl, benzyl and benzoyl radicals being optionally substituted on the phenyl ring by one or two substituents selected from fluorine, chlorine and bromine atoms and methyl, methoxy, methylthio, trifluoromethyl, hydroxyl and amino radicals.

A particular value for ring X is an oxazole, thiazole, imidazole, 1,2,4-thiadiazole, 1,2,4-oxadiazole, 1,2,3-triazole, 1,2,4-triazole, pyrazole, pyrazine, pyridine, pyrimidine or 1,3,5-triazine ring.

A particular value for the optional substituent on ring X when it is an alkyl, alkoxy or alkylthio radical is a methyl, methoxy or methylthio radical.

A particular value for —A— is a phenylene, cyclopentylene, cyclohexylene, methylene, ethylene, trimethylene, tetramethylene, pentamethylene, thiomethylene, thioethylene, thiotrimethylene, thiotetramethylene, thiopentamethylene, oxymethylene, oxyethylene, oxytrimethylene, oxytetramethylene, methylenethiomethylene, methylenethioethylene, methylenethiopropylene, methyleneoxymethylene, methyleneoxyethylene, ethyleneoxyethylene, oxy-2-methylethylene, thiopropylenethiomethylene, oxypropyleneoxy, oxyethyleneoxymethylene, oxyethylenethio, oxypropylenethio, iminomethylene, N-methyliminomethylene, iminoethylene, iminopropylene, vinylenepropylene, oxymethylenevinylene, 1,3-phenylene, 1,3-cyclopentylene, methylene-1,4-phenylene, ethyleneoxymethylene-1,4-phenylene, oxy-1,3-phenylenemethylene or thiomethyleneethynylenemethylene radical. These values for —A— are written reading from left to right in formula I such that the first named part of the radical is attached to ring X and the last named part of the radical is attached to $CR^3R^4$. Thus, for example, when —A— is an oxyethylene radical, the compound of the formula I contains the part structure III:

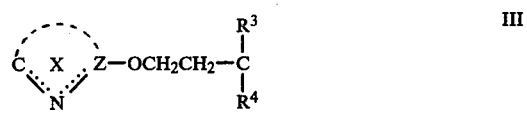

A particular value for $R^3$ is a hydrogen atom or a methyl, cyclohexyl, cyclopropyklmethyl, allyl, propargyl or 2-methoxyethyl radical.

A particular value for $R^4$ is a hydrogen atom or a methyl radical.

A particular value for $A—CR^3R^4$ is an oxy-1,4-cyclohexylene radical.

A particular value for $R^5$ is a hydrogen atom or a methyl, acetyl, phenyl, benzyl or benzoyl radical, the phenyl, benzyl and benzoyl radicals being optionally substituted by one or two substituents selected from fluorine, chlorine and bromine atoms and methyl, methoxy, methylthio, cyano, trifluoromethyl, hydroxy and amino radicals.

The following are 9 preferred features of the guanidine derivative of the formula I. When any one of these features is taken, either singly or in combination, with the other general or particular features of the guanidine derivative of the formula I listed above, there are obtained preferred sub groups of compounds within the above general definition.

1. $R^2$ is a hydrogen atom and $R^1$ is a 2,2,2-trifluoroethyl, 2,2,3,3-tetrafluoropropyl, ethyl, propyl, benzoyl or phenyl radical.

2. $R^2$ is a hydrogen atom and $R^1$ is a 2,2,2-trifluoroethyl, 2,2,2,3,3-tetrafluoropropyl or propyl radical.

3. The optional substituent on ring X is a fluorine or bromine atom.

4. Ring X carries no optional substituent.

5. Ring X is a pyrazole, 4-fluoropyrazole, 4-bromopyrazole, thiazole in which A is linked at the 4-position, 1,2,3-triazole, 1,2,4-triazole, pyrimidine in which A is linked at the 2-position, pyridine or pyrazine ring.

6. Ring X is a 4-fluoropyrazole, 1,2,3-triazole or pyrimidine in which A is linked at the 2-position, ring.

7. A is an oxyethylene, iminoethylene or trimethylene radical.

8. D is an oxygen atom.

9. $R^3$, $R^4$ and $R^5$ are hydrogen atoms.

Particular compounds of the invention are set out in the Examples. The following is a preferred group of compounds:

4-[2-(2,2,2-trifluoroethyl)guanidino]-2-(3-hydroxypropoxy)pyrimidine (Example 1);
4-fluoro-1-(4-hydroxybutyl)-3-[2-(2,2,2-trifluoroethyl)guanidino]pyrazole (Example 7);
2-(4-hydroxybutyl)-4-[2-(2,2,2-trifluoroethyl)guanidino]pyrimidine (Example 14);
4-[2-(2,2,2-trifluoroethyl)guanidino]-2-(3-hydroxypropylamino)pyrimidine (Example 21);
4-[2-(2,2,3,3-tetrafluoropropyl)guanidino]-2-(3-hydroxypropoxy)pyrimidine (Example 24);
4-(2-propylguanidino)-2-(3-hydroxypropoxy)pyrimidine (Example 31);
4-[2-(2,2,2-trifluoroethyl)guanidino]-2-(4-hydroxybutyl)-1,2,3-triazole (Example 38);
and the pharmaceutically-acceptable acid-addition salts thereof.

Of this group particularly preferred compounds are those of Examples 21, 24 and 31.

A suitable pharmaceutically-acceptable acid-addition salt of the guanidine derivative of the formula I is, for example, a salt formed with hydrochloric, hydrobromic, phosphoric, sulphuric, acetic, citric or maleic acid.

The guanidine derivative of the invention may be manufactured by methods in which the actual chemical reactions involved are known in themselves. The following processes, $R^1$, $R^2$, $R^3$, $R^4$, $R^5$, A, D and ring X having the meanings stated above, unless indicated otherwise, are therefore provided as further features of the invention.

The process of the invention is characterized by:

(a) Construction of the guanidine radical attached to ring X by reaction of the appropriate thiourea, or a 1–6C S-alkyl or S-benzyl derivative thereof, or a salt of such a derivative, with the appropriate amine. The guanidine radical in the compound of the formula I contains three nitrogen atoms each of which carries different substituents. The appropriate amine for use in this reaction may therefore be ammonia, an amine of the formula $R^1R^2NH$ or an amine of the formula IV:

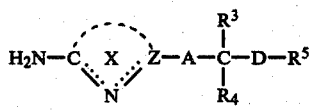
                                                    IV

The reaction may be conducted using an excess of one of the reactants as a diluent or solvent, or an additional diluent or solvent, for example methanol or ethanol, may be used. In many cases it is advantageous to use a catalyst such as mercuric oxide, lead oxide or sodium hypochlorite. The reaction may be conducted at ambient temperature, or it may be accelerated or completed by the application of heat, for example by heating to the boiling point of the diluent or solvent.

(b) For those compounds in which the group inserted into A is an oxygen or sulphur atom or an NH or N-alkyl radical, reaction of a compound of the formula V or VI:

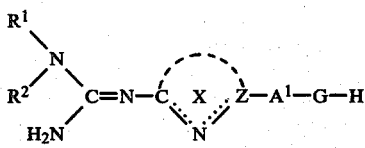
                                                    V

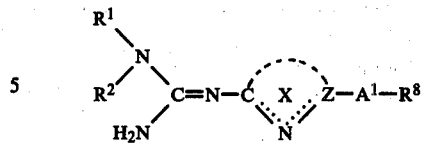
                                                    VI with the compound of the formula VII or VIII respectively:

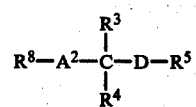
                                                    VII

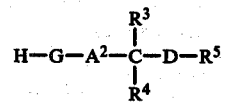
                                                    VIII in which G is an oxygen or sulphur atom or an NH or N-alkyl radical, $R^8$ is a displaceable radical and $A^1$ and $A^2$ are fragments of A, including direct bonds, and are such that $A^1$—G—$A^2$ falls within the definition of A given above. $R^8$ is, for example a halogen atom, for example a chlorine, bromine or iodine atom. When $R^8$ is directly attached to ring X, $R^8$ is, for example, a methylsulphinyl or methylsulphonyl radical.

(c) For those compounds in which the optional substituent on ring X is a halogen atom, halogenation of the corresponding unsubstituted compound. When the substituent is a bromine atom a suitable reagent is bromine in a diluent or solvent such as chloroform. When the substituent is a fluorine atom a suitable reagent is trifluoromethylhypofluorite in a diluent or solvent such as aqueous trifluoroacetic acid.

(d) For those compounds in which $R^5$ is an alkyl, alkanoyl, aryl, arylalkyl or aroyl radical, reaction of the corresponding compound in which $R^5$ is a hydrogen atom with a compound of the formula IX:

$$R^9\text{—}R^8 \qquad\qquad\qquad IX$$

in which $R^9$ is a 1–6C alkyl, 1–6C alkanoyl, 6–10C aryl, 7–11C arylalkyl or 7–11C aroyl radical and $R^8$ is a displaceable radical. $R^8$ is, for example, a chlorine or bromine atom. When $R^9$ is an alkanoyl or aroyl radical $R^8$ may also be the corresponding alkanoyloxy or aroyloxy radical.

(e) For those compounds in which $R^5$ is a hydrogen atom, replacement of hydrogen of the replaceable radical $R^{10}$ in a compound of the formula X:

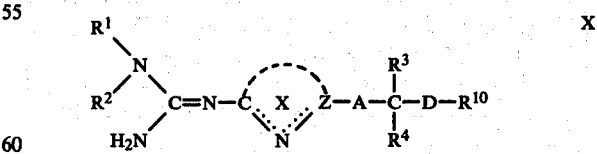
                                                    X $R^{10}$ is, for example, an optionally-substituted benzyl, 1–6C alkanoyl or 7–10C aroyl radical, for example a benzyl, acetyl or benzoyl radical. When $R^{10}$ is an optionally-substituted benzyl radical it may be replaced by hydrogen by hydrogenolysis, for example in the presence of a palladium on charcoal catalyst and in a diluent or solvent such as water, methanol or ethanol. When $R^{10}$ is an alkanoyl or aroyl radical it may be replaced by hydrogen by hydrolysis, for example with a base such as sodium or potassium hydroxide.

(f) For those compounds in which $R^4$ and $R^5$ are hydrogen atoms, reduction of a compound of the formula XI:

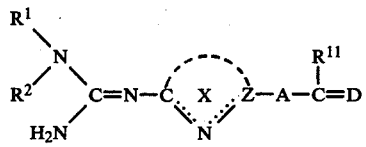

XI in which $R^{11}$ is a hydrogen atom or a 1-6C alkyl, 3-8C cycloalkyl, 4-12C cycloalkylalkyl, 3-6C alkenyl, 3-6C alkynyl, 2-8C alkoxyalkyl, hydroxy or 1-6C alkoxy radical. The reducing agent may, for example, be a complex metal hydride such as lithium aluminum hydride or sodium borohydride. The reaction may be conducted in a diluent or solvent such as tetrahydrofuran or diethyl ether, and may be accelerated or completed by the application of heat, for example by heating to the boiling point of the diluent or solvent.

(g) For those compounds in which ring X is a thiazole ring, reaction of a compound of the formula XII:

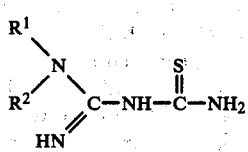

XII with a compound of the formula XIII:

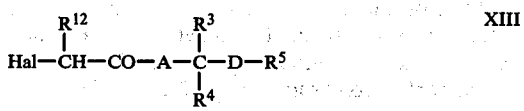

XIII in which Hal is a chlorine or bromine atom and $R^{12}$ is a hydrogen atom or the optional substituent on the thiazole ring. The reaction may be conducted in a diluent or solvent such as acetone and may be accelerated or completed by the application of heat, for example by heating to the boiling point of the diluent or solvent.

(h) Construction of the guanidine radical attached to ring X by reaction of the appropriate cyanamide with the appropriate amine. Since the guanidine radical in the compound of the formula I contains only one unsubstituted nitrogen atom, there are two appropriate amines, namely the amine of the formula $R^1R^2NH$ or of the formula IV given above.

(i) For those compounds in which Z is a nitrogen atom, reaction of a compound of the formula XIV:

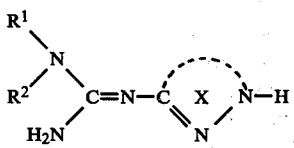

XIV with a compound of the formula XV:

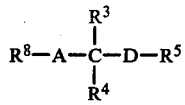

XV in which $R^8$ is a displaceable radical. $R^8$ is, for example, a halogen atom, for example a chlorine or bromine atom.

(j) For those compounds in which $R^5$ is a hydrogen atom and $R^3$ is other than a hydrogen atom, reaction of a compound of the formula XVI:

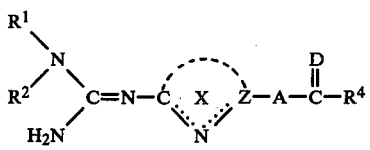

XVI with a compound of the formula $R^{13}$—Mg—$R^{14}$, $R^{13}$—Li or $R_2^{13}$Mg in which $R^{13}$ is a 1-6C alkyl, 3-8C cycloalkyl, 4-12C cycloalkylalkyl, 3-6C alkenyl, 3-6C alkynyl or 2-8C alkoxyalkyl radical and $R^{14}$ is a chlorine, bromine or iodine atom. The reaction may be conducted in a diluent or solvent such as diethyl ether or tetrahydrofuran.

When the process of the invention manufacturers the compound of the formula I in the form of the free base, and an acid-addition salt is required, the compound of the formula I in the free base form is reacted with an acid which affords a pharmaceutically-acceptable anion.

The starting material of the formula IV for use in process (a) may be prepared by construction of the right hand side chain on the appropriate ring X. The method of construction may vary depending on the nature of ring X, the nature of the atom Z in ring X to which A is attached (carbon or nitrogen) and the presence of or absence of inserted atoms or groups in chain A. When A contains no inserted atom or group or the inserted group is a phenylene or cycloalkylene radical and Z is a carbon atom, it is preferable to construct the ring X with the right hand side chain already in place. Thus when ring X is a thiazole ring, a process similar to that described in process (g) may be used. When ring X is a 1,2,3-triazole ring, it may be formed by reaction of methazonic acid with a suitable azide, followed by reducing of the nitro group to an amino group, for example as illustrated in Example 37. When ring X is a pyrimidine ring, it may be formed by reaction of a suitably substituted amidine with 2-chloroacrylonitrile, for example as illustrated in Examples 13 and 14. When ring X is a pyrazole ring it may be formed by reaction of a suitably-substituted hydrazide with 2-chloroacrylonitrile, for example as illustrated in Examples 5, 9 and 10. When the inserted group in A is an oxygen or sulphur atom or a vinylene, ethynylene, cycloalkylene, NH or N-alkyl radical, A may be introduced onto an existing ring X. Thus when the inserted group is a vinylene or ethynylene radical A may be introduced by formulation of the double or triple bond by standard coupling methods. When the inserted group in A is a cycloalkylene radical, the chain A may be constructed by a conjugate addition to the corresponding cycloalk-2-enone. When the inserted group in A is an oxygen or sulphur atom or an NH or N-alkyl radical, the chain may be built up by a method similar to that described in process (b), for example as illustrated in Examples 3, 15, 16, 17, 19, 20 and 35. When Z is a nitrogen atom, the side chain may be formed by a method similar to that described in process (i), for example as illustrated in Example 38. The thiourea corresponding to the compound of the formula IV for use in process (a) may be prepared by reaction of the compound of the formula IV with $R^1R^2N=C=S$, for example as illustrated in Examples 3, 4, 5, 8, 9, 10, 11, 13, 14, 15, 16, 17, 19, 20, 35, 37 and 38.

The starting materials of the formula V and VI for use in process (b), and of the formula XIV for use in process (i), may be prepared by construction of the guanidine chain on a suitably substituted ring X, for example as illustrated in Examples 31, 32 and 36.

The starting material of the formula XI for use in process (f) and of the formula XVI for use in process (j) may be prepared by methods exactly analogous to processes (a), (b), (c), (g), (h) or (i), for example as illustrated in Examples 33 and 34.

The cyanamide, corresponding to the amine of the formula IV, for use in process (h) may be prepared by reaction of the compound of the formula IV with cyanogen bromide.

As noted above, the guanidine derivative of the invention is a histamine H-2 antagonist, inhibits the secretion of gastric acid in warm-blooded animals and is therefore useful in the treatment of peptic ulcers and other conditions caused or exacerbated by gastric acidity, including stress ulcers and gastrointestinal bleeding due to trauma.

The histamine H-2 antagonist activity may be demonstrated on standard tests, for example by the ability of the compound of the formula I to inhibit the histamine-induced positive chronotropic response in the spontaneously beating right atrium of the guinea pig or by its ability to inhibit the histamine-induced uptake of aminopyrine into the acid space of parietal cells.

The guinea pig atrium test is carried out as follows:

A guinea pig right atrium is suspended at 1 g. tension (isometric) in a thermostatically-controlled (30° C.) tissue bath (25 ml.) containing oxygenated (95% $O_2$, 5% $CO_2$) Krebs-Henseleit buffer (pH 7.4). The tissue is allowed to stabilise over 1 hour during which time it is washed 2-4 times. Individual contractions are recorded with a force-displacement transducer through a strain gauge coupler, and instantaneous rates are monitored with a cardiotachometer. A control response to 1 $\mu$M histamine is obtained after which the tissue is washed 3 times and allowed to re-equilibrate to basal rate. After re-equilibration for 15 minutes, the test compound is added to the desired final concentration. Ten minutes after addition to the compound histamine (1 $\mu$M) is again added and the response to histamine in the presence of antagonist is compared to the histamine control response. The result is expressed as a percentage of the histamine control response. Thereafter the apparent dissociation constant of the H-2 antagonist is determined by standard procedures.

The aminopyrine test is carried out as follows:

Gastric mucosa from the New Zealand white rabbit is removed from the underlying muscle and washed in Buffer 1 [containing per liter NaCl; (8.007 g.), KCl (0.201 g.), $Na_2HPO_4$ (0.113 g.), $KH_2PO_4$ (0.204 g.), $CaCl_2.2H_2O$ (0.132 g.), $MgCl_2$ (0.101 g.) and glucose (1 g.), adjusted to pH 7.4 with NaOH]. The tissue is finely chopped, suspended in Buffer 1 and washed three times with Buffer 1. The tissue is then suspended in dispersion medium [collagenase (Sigma Chemical Co., Type V; 100 mg.) and bovine serum albumin (Miles Laboratories Ltd., Fraction V; 100 mg.) in Buffer 1 (100 ml.); 50 ml. per 10 g. net weight of tissue] and incubated at 30° C. and pH 7.4 (maintained by continuous monitoring) with stirring under an oxygen atmosphere. After 30 minutes the tissue is allowed to settle and the supernatant liquid is removed. Fresh dispersion medium (50 ml. per 10 g. wet weight of tissue) is added and incubation is continued with the tissue being largely dispersed into glands and whole cells after 40-60 minutes. Any remaining large pieces of tissue are removed by filtration through nylon mesh. The mixture of glands and cells is collected by centrifugation at 200×g. and suspended in Buffer 1 containing 1% bovine serum albumin (Miles Laboratories Ltd., Fraction V). Finally the cells and glands are washed 3 times with Buffer 1 and suspended in Buffer 2 [containing Eagles MEM (500 ml.), Aprotinin (Sigma Chemical Co., 10 mg.) and HEPES (2-[4-(2-hydroxyethyl)piperazin-1-yl]ethanesulphonic acid; 150 mM., 20 ml.) adjusted to pH 7.4 with NaOH; 150 ml. per 10 g. net weight of tissue]. The tissue suspension is stirred under an oxygen atmosphere at 32° C. for at least 1 hour before use. The tissue suspension is incubated with the test compound and aminopyrine (10 $\mu$M) labelled with $C^{14}$ on the dimethylamino group (0.1 $\mu$Ci/ml.) for 20 minutes. The uptake of the aminopyrine is then stimulated by addition of histamine and the phosphodiesterase inhibitor ICI 63197 (*Biochem.Soc.Special Publication* 1, 1973, pp 127-132) to final concentrations of $10^{31\ 5}$ M. and $5\times10^{-7}$ M. respectively. After 18 minutes the cells/glands are separated from the incubation medium by filtration of the suspension through glass microfibre filters. The cells/glands are quickly (<10 seconds) washed three times with ice-cold Buffer 1. The $C^{14}$ aminopyrine retained by the tissue is measured on a scintillation counter and the degree of inhibition of uptake by the test compound is calculated by reference to a control sample. The concentration of test compound giving 50% inhibition is then calculated graphically from a series of tests run at different concentrations.

All the compounds exemplified in this specification were tested either on the guinea pig atrium test or on the aminopyrine test. All those tested on the guinea pig atrium test are active at or below a bath concentration of 10 $\mu$M. and the more active compounds show complete inhibition of response at this concentration. All those tested on the aminopyrine test gave a 50% inhibition of uptake of aminopyrine at or below a concentration of 3 $\mu$M.

The inhibition of the secretion of gastric acid may be demonstrated in standard tests, for example by the ability of the compound of the formula I, when dosed intravenously, intragastrically or orally, to inhibit the secretion of acidic gastric juice in, for example, rats, or dogs provided with gastric fistulae or denervated fundic pouches, and whose gastric secretion is stimulated by administration of a secretagogue, for example histamine, pentagastrin, bethanechol or food.

The test in rats is carried out as follows:

Female rats (200-230 g.) are anesthetized by intramuscular administration of urethane (1.5 g/kg.) and the trachea cannulated. A soft tube is passed down the oesophagus into the stomach and secured by a tie in the neck region. A multi-orifice plastic tube (3 mm. diameter) is passed into the antral region of the stomach, via an incision in the duodenum, and tied in place by means of a ligature around the pylorus. Saline (9 g./l. NaCl) is perfused through the stomach via the oesophageal cannula at a rate of 7 ml./minute and collected into beakers from the pyloric outlet over periods of 10 minutes. Acid secretion is stimulated by subcutaneous administration of the specific H-2 agonist dimaprit in a loading dose of 10 mg./kg. followed by an infusion of 30 mg./kg./hour. Acid output is computed by titration of the 10 minute samples to an end point of pH 6.4 with 20 mM. NaOH. When secretion has reached a plateau (three consecutive readings within 5%) the test compound is administered intravenously via a cannula placed in the left external jugular vein. Secretion is then measured for a further 2 hours. A stock solution of each test compound is prepared (10 mg./ml. in DMSO) and appropriate dilution made with saline to enable injection in a dose volume of 1 ml/kg. (DMSO <2%).

The test in dogs provided with chronic fistulae is carried out as follows:

A female pure bred beagle (9–12 kg.) having a chronic gastric fistula is fasted overnight with water ad lib. During the experiment the dog is lightly restrained in a standing position. When studying the test compound by the intravenous route, the fistula is opened and, after ascertaining the absence of basal secretion over a period of 30 minutes, a continuous intravenous infusion of secretagogue (0.5 μmol/kg/hour of histamine or 2 μg./kg./hour pentagastrin) in saline (15 ml./hour) is begun. Gastric acid samples are collected every 15 minutes. The volume of each sample is measured and a 1 ml. aliquot is titrated to neutrality with 100 mM NaOH to determine acid concentration. When a plateau of secretion is reached (1–2 hours), the test compound is administered intravenously in saline and gastric acid samples are collected for a further 2–3 hours during which time the infusion of the secretagogue continues uninterrupted.

When studying the test compound by the intragastric route, the absence of basal secretion over a period of 30 minutes is ascertained and the test compound, contained in 25 ml. of 0.5% w/v hydroxypropyl methylcellulose and 0.1% w/v 'Tween' 80 in water ('Tween' is a Trade Mark) is instilled into the stomach through a fistula dosing plug. One hour later, the fistula is reopened and intravenous infusion of a secretagogue, as described above, is immediately begun. Gastric acid samples are measured as described above and the approach of acid secretion to a plateau is compared to that of a control animal which is dosed intragastrically only with the dosing vehicle.

When studying the test compound by the oral route it is administered in a gelatin capsule with 15 ml. of water. One hour later, the fistula is opened and intravenous infusion of the secretagogue is immediately begun. Gastric acid samples are measured as above and the approach of acid secretion to a plateau is compared to that of an undosed control animal.

The test in dogs provided with denervated fundic pouches is carried out as follows:

Male beagle dogs (14–22 kg.) are prepared with vagally denervated pouches of the fundic gland area by the method of Rudick et al. (*J.Surg.Res.* 1967, 7 383.) The animals are allowed 4–6 weeks to recover from surgery and a further period of 2–3 months prior to routine use, to allow for table training and standardization of secretory responses. The dogs are starved for 23 hours before use (water ad lib) and during experiments they are lightly restrained in cloth slings. After rinsing the pouch with warm water, histamine is infused subcutaneously at a rate of 10 μg./minute. This dose of agonist produces a submaximal (60–90% of maximum) increase in acid output in all dogs used. Pouch secretions are collected over 15 minute periods into graduated glass test-tubes and the volume measured to the nearest 0.1 ml. A 500 μl sample is diluted with 5 ml. of saline and titrated to pH 7.0 with 100 mM NaOH. Total acid output is computed from the product of acid concentration and volume of juice secreted. Compounds are administered intravenously (0.1 ml./kg.) via a cephalic vein or orally in a gelatin capsule when a secretory plateau (3 consecutive readings within 10%) has been attained. Secretion is measured for a period of 3 hours following administration of test compound.

The results obtained in the atrium and aminopyrine tests are predictive of activity in the rat and dog tests.

The compound 4-[2-(2,2,2-trifluoroethyl)guanidino]-2-(3-hydroxypropoxy)pyrimidine had an $LD_{50}$ in mice, dosed intravenously, of approximately 30 mg./kg.

The N-methylcyanoguanidine group in known H-2 receptor antagonists is potentially changeable into the carcinogenic N-nitroso N-methylcyanoguanidine group in the mammalian body (Pool et al., *Toxicology*, 1975, 15, 69). The corresponding group in the compounds of the present invention, $-D-R^5$, is not potentially changeable into carcinogenic nitroso derivatives.

According to a further feature of the invention there is provided a pharmaceutical composition which comprises a guanidine derivative of the invention in association with a non-toxic pharmaceutically-acceptable diluent or carrier.

The pharmaceutical composition may, for example, be in a form suitable for oral, rectal, parenteral or topical administration, for which purposes it may be formulated by means known to the art into the form of, for example, tablets, capsules, aqueous or oily solutions or suspension, emulsions, dispersible powders, suppositories, sterile injectable aqueous or oily solutions or suspensions, gels, creams, ointments or lotions.

In addition to the guanidine derivative of the formula I, the pharmaceutical composition of the invention for oral, rectal or parenteral administration may also contain, or be co-administered with, one or more known drugs selected from antacids, for example aluminium hydroxide-magnesium hydroxide mixtures; antipepsin compounds, for example pepstatin; other histamine H-2 antagonists, for example cimetidine or ranitidine; ulcer healing agents, for example carbenoxolone or bismuth salts; anti-inflammatory agents, for example ibuprofen, indomethacin, naproxen or aspirin prostaglandins, for example 16,16-dimethylprostaglandin $E_2$; classical antihistamines (histamine H-1 antagonists), for example mepyramine or diphenhydramine; anticholinergic agents, for example atropine or propantheline bromide; anxiolytic agents, for example diazepam, chlordiazepoxide or phenobarbital.

The pharmaceutical composition of the invention for topical administration may also contain, in addition to the guanidine derivative, one or more classical anti-histamines (histamine H-1 antagonists), for example mepyramine or diphenhydramine and/or one or more steroidal anti-inflammatory agents, for example fluocinolone or triamcinolone.

A topical formulation may contain 1–10% w/w of the guanidine derivative of the invention. A preferred pharmaceutical composition of the invention is one suitable for oral administration in unit dosage form, for example a tablet or capsule which contains between 5 mg. and 500 mg. of the guanidine derivative, or one suitable for intravenous, subcutaneous or intramuscular injection, for example a sterile injectable containing between 0.1% and 10% w/w of the guanidine derivative.

The pharmaceutical composition of the invention will normally be administered to man for the treatment of peptic ulcers and other conditions caused or exacerbated by gastric acidity in the same general manner as that employed for cimetidine, due allowance being made in terms of dose levels for the potency and duration of action of the guanidine derivative of the present invention relative to cimetidine. Thus each patient will receive an oral dose of between 15 mg. and 1500 mg., and preferably between 10 mg. and 100 mg., of guanidine derivative or an intravenous, subcutaneous or intramuscular dose of between 1.5 mg. and 150 mg., and preferably between 5 mg. and 20 mg., of the guanidine derivative, the composition being administered 1 to 4 times, and preferably once, per day. The rectal dose will be approximately the same as the oral dose. The composition may be administered less frequently when it contains an amount of guanidine derivative which is a multiple of the amount which is effective when given 1–4 times per day.

The invention is illustrated, but not limited, by the following Examples. The n.m.r. spectra are quoted in δ relative to tetramethylsilane (δ=0) as internal standard (s=singlet, d=doublet, t=triplet, q=quartet, m=multiplet, br=broad). The temperatures are in degrees Centigrade. The following contractions are used:
HOAc=acetic acid
DMF=dimethyl formamide
ether=diethyl ether
DMSO=dimethylsulphoxide
MeOH=methanol
EtOH=ethanol
THF=tetrahydrofuran
EtOAc=ethyl acetate Attention is drawn to the fact that 4-nitrotriazole (Example 38) is an explosion hazard.

EXAMPLE 1

A 50% w/w dispersion of sodium hydride in oil (48 mg.) was added to propane-1,3-diol (0.5 ml.) and the mixture stirred at room temperature for 0.5 hours. 4-[2-(2,2,2-Trifluoroethyl)guanidino]-2-methanesulphonylpyrimidine (0.15 g.) was added and the mixture heated at 90° with occasional shaking for 0.5 hours and then cooled to room temperature. The mixture was taken up in N aqueous HCl and washed with EtOAc. The aqueous phase was basified with 10 N aqueous NaOH and then extracted three times with EtOAc. The combined extracts were dried and evaporated to dryness. A solution of the residue in acetone was added to a solution of maleic acid in acetone, and the precipitate collected to give 4-[2-(2,2,2-trifluoroethyl)guanidino]-2-(3-hydroxypropoxy)pyrimidine hydrogen maleate (0.19 g.), m.p. 165°–166° (after recrystallisation from EtOH).

The 4-[2-(2,2,2-trifluoroethyl)guanidino]-2-methylsulphonylpyrimidine used as starting material may be obtained as follows:

A suspension of 4-[2-(2,2,2-trifluoroethyl)guanidino]-2-methylthiopyrimidine (5.3 g.) in chloroform (500 ml.) was treated with 3-chloroperbenzoic acid (12 g., 85% w/w) and the solution left at room temperature for 18 hours. The mixture was washed twice with a solution of a mixture of potassium carbonate (10 g.) and sodium sulphite (2 g.) in water (50 ml.), and then dried and evaporated to dryness. The residue was fractionated by medium pressure liquid chromatography on Merck "Kieselgel 60" to give 4-[2-(2,2,2-trifluoroethyl)guanidino]-2-methylsulphonylpyrimidine (2.2 g.), m.p. 158°–159° (after recrystallisation from EtOH).

EXAMPLE 2

By a similar process to that in Example 1, using butane-1,4-diol in place of propane-1,3-diol, there was obtained 4-[2-(2,2,2-trifluoroethyl)guanidino]-2-(4-hydroxybutoxy)pyrimidine hydrogen maleate, m.p. 189°–190°.

EXAMPLE 3

A mixture of 6-[3-(2,2,2-trifluoroethyl)thioureido]-2-(3-hydroxypropoxy)pyridine (0.15 g.), saturated ethanolic ammonia (1 ml.), MeOH (20 ml.) and yellow mercuric oxide (0.25 g.) was stirred at room temperature for 2 hours and then filtered. The filtrate was evaporated to dryness, and the residue dissolved in EtOAc and added to a solution of maleic acid in acetone. The precipitate was collected to give 6-[2-(2,2,2-trifluoroethyl)guanidino]-2-(3-hydroxypropoxy)pyridine hydrogen maleate, m.p. 174°–175°.

The 6-[3-(2,2,2-trifluoroethyl)thioureido]-2-(3-hydroxypropoxy)pyridine used as starting material may be obtained as follows:

A 50% w/w dispersion of sodium hydride in oil (0.5 g.) was added in portions to propane-1,3-diol (5 ml.) and the mixture stirred at room temperature for 1 hour. 2-Amino-6-bromopyridine (0.85 g.) was added and the mixture stirred at 150° for 4 hours and then cooled to room temperature. The mixture was taken up in N aqueous HCl and washed with EtOAc and the aqueous phase basified with 10 N aqueous NaOH. The mixture was extracted three times with EtOAc and the combined extracts dried and evaporated to dryness to give a brown oil (1.6 g.). A portion of the oil (0.67 g.) was dissolved in acetonitrile (5 ml.) and the solution treated with 2,2,2-trifluoroethylisothiocyanate (0.3 g.). The mixture was kept at room temperature for 18 hours and then evaporated to dryness and the residue recrystallised from EtOH to give 6-[3-(2,2,2-trifluoroethyl)thioureido]-2-(3-hydroxypropoxy)pyridine (0.18 g.), m.p. 123°–124°.

EXAMPLE 4

By a similar process to that described in Example 3, there was obtained 6-(2-ethylguanidino)-2-(3-hydroxypropoxy)pyridine hydrogen maleate, m.p. 140°–141°.

EXAMPLE 5

Yellow mercuric oxide (30.1 g.) was added quickly to a stirred solution of 1-(4-hydroxybutyl)-3-[3-(2,2,2-trifluoroethyl)thioureido]pyrazole (10.4 g.) in methanolic ammonia (5 M; 340 ml.). After stirring for 3 hours at room temperature, the reaction mixture was filtered through diatomaceous earth and the filtrate evaporated to dryness in vacuo to give 1-(4-hydroxybutyl)-3-[2-(2,2,2-trifluoroethyl)guanidino]pyrazole, m.p. 105°–106° (yield 82%).

The starting material may be prepared as follows:
2-Chloroacrylonitrile (12.2 g.) was added slowly to a mixture of 4-hydroxybutylhydrazine (16.1 g.) in water (60 ml.) containing potassium carbonate (21.2 g.). After the resulting exotherm had subsided, the reaction mixture was stirred at room temperature for three hours, then extracted continuously with ether for three days. On evaporation of the ether in vacuo 3-amino-1-(4-hydroxybutyl)pyrazole was obtained as a thick brown oil (96% yield).

To a solution of 3-amino-1-(4-hydroxybutyl)pyrazole (22 g.) in dry acetonitrile (60 ml.) was added 2,2,2-trifluoroethylisothiocyanate (20.9 g.) slowly over 5 minutes. After stirring for a further 17 hours the solvent was evaporated in vacuo to give a thick brown oil which, on purification by column chromatography on silica gel using EtOAc as eluant, gave 1-(4-hydroxybutyl)-3-[3-(2,2,2-trifluoroethyl)thioureido]pyrazole, m.p. 94°–96° (after recrystallisation from EtOAc/petroleum ether [b.p. 40°–60°]) (yield 38%).

EXAMPLE 6

A solution (2.75 ml.) of bromine (80 mg.) in chloroform was added to a solution of 1-(4-hydroxybutyl)-3-[2-(2,2,2-trifluoroethyl)guanidino]pyrazole (140 mg.) in HOAc (2 ml.). After stirring at room temperature for 1 hour the mixture was basified with 6 N aqueous ammonium hydroxide and then extracted with EtOAc (6×10 ml.). The combined extracts were dried (MgSO$_4$) and evaporated to dryness in vacuo to give 4-bromo-1-(4-hydroxybutyl)-3-[2-(2,2,2-trifluoroethyl)guanidino]-pyrazole (145 mg., 82%) having the following n.m.r. spectrum in d$_6$DMSO: 7.7 (s, 1H); 4.2 (br t, 2H); 3.9 (t, 2H); 3.3 (t, 2H); 1.5 (br m, 4H).

EXAMPLE 7

Trifluoromethylhypofluorite (20 ml. measured by gas burette) was bubbled (assisted by a nitrogen pump) into a solution of 1-(4-hydroxybutyl)-3-[2-(2,2,2-trifluoroethyl)guanidino]pyrazole (100 mg.) in a mixture of trifluoroacetic acid (2 ml.) and water (2 ml.), cooled to −20° and under nitrogen. The reaction was stirred at −20° for 2.5 hours, then basified with concentrated ammonium hydroxide solution. Extraction with EtOAc (4×10 ml.), drying (MgSO$_4$) and evaporation in vacuo gave 4-fluoro-1-(4-hydroxybutyl)-3-[2-(2,2,2-trifluoroethyl)guanidino]pyrazole (80 mg., 76%) having the following n.m.r. spectrum in d$_6$DMSO: 7.6 (d, 1H); 4.1 (m, 2H); 3.8 (t, 2H); 3.4 (t, 2H); 1.75 (m, 2H); 1.4 (m, 2H).

EXAMPLE 8

A mixture of 1-(4-hydroxybutyl)-3-(3-benzoylthioureido)pyrazole (0.58 g.) and yellow mercuric oxide (1.5 g.) in methanolic ammonia (6 M; 15 ml.) was stirred for three days. The slurry was clarified by centrifuging and the supernatant liquor evaporated in vacuo to an oil. The oil was purified by column chromatography on silica gel using MeOH/EtOAc 1:9 v/v as eluant. The product in MeOH was treated with a saturated aqueous solution of picric acid to give 3-(2-benzoylguanidino)-1-(4-hydroxybutyl)pyrazole picrate, m.p. 147°–148° (14% yield).

The starting material may be prepared as follows:

A mixture of 3-amino-1-(4-hydroxybutyl)pyrazole (0.966 g.) and benzoylisothiocyanate (1.0 g.) in acetone (30 ml.) was stirred at room temperature for 18 hours. The solvent was evaporated and the residue purified by column chromatography on silica gel using EtOAc as eluant to give 1-(4-hydroxybutyl)-3-(3-benzoylthioureido)pyrazole (30% yield).

EXAMPLES 9–10

The process of Example 5 was repeated using 1-(3-hydroxypropyl)-3-[3-(2,2,2-trifluoroethyl)thioureido]pyrazole and 1-(2-hydroxyethyl)-3-[3-(2,2,2-trifluoroethyl)thioureido]pyrazole as starting materials. There were thus obtained 1-(3-hydroxypropyl)-3-[2-(2,2,2-trifluoroethyl)guanidino]pyrazole picrate, m.p. 157° (yield 95%) and 1-(2-hydroxyethyl)-3-[2-(2,2,2-trifluoroethyl)guanidino]pyrazole, m.p. 81°–82° (yield 95%), respectively.

The starting materials may be prepared by repeating the second and third parts of Example 5 using 3-hydroxypropylhydrazine and 2-hydroxyethylhydrazine respectively in place of 4-hydroxybutylhydrazine.

EXAMPLE 11

Yellow mercuric oxide (0.295 g.) was added to a solution of 1-(4-hydroxybutyl)-3-(3-phenylthioureido)pyrazole (100 mg.) in ethanolic ammonia (6 M; 10 ml.). The mixture was stirred at room temperature for 48 hours, centrifuged to remove the precipitated mercuric sulphide, and the supernatant evaporated to dryness in vacuo to give 1-(4-hydroxybutyl)-3-(2-phenylguanidino)pyrazole (98 mg; 100%) having the following n.m.r. spectrum in d$_6$DMSO: 7.3 (br m, 9H); 5.7 (d, 1H); 4.2 (br m, 1H); 3.9 (t, 2H); 3.3 (t, 2H); 1.5 (br m, 4H).

The starting material may be prepared as follows:

To a solution of 3-amino-1-(4-hydroxybutyl)pyrazole (1.0 g.) in dry acetonitrile (3 ml.) was slowly added phenylisothiocyanate (0.95 g.) and the mixture was stirred at room temperature for 17 hours. The solvent was evaporated and the residue purified by column chromatography on silica gel using EtOAc as eluant to give 1-(4-hydroxybutyl)-3-(3-phenylthioureido)pyrazole (0.54 g.; 29%), m.p. 112°–117°.

EXAMPLE 12

A mixture of 1-(2-hydroxyethyl)-3-[2-(2,2,2-trifluoroethyl)guanidino]pyrazole (2.5 g.) and 4-cyanobenzyl bromide (1.96 g.) was heated at 140° for 10 minutes. When cool, the residue was dissolved in a little MeOH and purified by medium pressure chromatography on silica gel using triethylamine/EtOH/EtOAc 1:10:95 v/v/v as eluant to give 1-[2-(4-cyanobenzyloxy)ethyl]-3-[2-(2,2,2-trifluoroethyl)guanidino]pyrazole (yield 55%) having the following n.m.r. spectrum in d$_6$DMSO: 7.5 (br m, 5H); 5.85 (d, 1H); 5.1 (s, 2H); 4.05 (br m, 4H); 3.7 (br t, 2H).

EXAMPLE 13

A solution of 2-(3-benzyloxypropyl)-4-[2-(2,2,2-trifluoroethyl)guanidino]pyrimidine (3.7 g.) in EtOH (75 ml.) containing concentrated aqueous HCl (1 ml.) was hydrogenated over 5% w/w palladium on carbon (1 g.). The filtrate was evaporated and the residue was partitioned between dilute aqueous NaOH and EtOAc. The EtOAc solution was washed with brine, dried and evaporated and the residue was crystallised from EtOAc to give 2-(3-hydroxypropyl)-4-[2-(2,2,2-trifluoroethyl)guanidino]pyrimidine (0.2 g.), m.p. 136°–138°.

The starting material may be obtained as follows:

A solution of 4-benzyloxybutyronitrile (16.5 g.) and EtOH (8.6 g.) in CH$_2$Cl$_2$ (100 ml.) was saturated with HCl gas at 0° and the mixture kept at 0° for 6 days. The resulting suspension was evaporated to dryness in vacuo and the residue was slurried with dry ether. The insoluble solid was added to 40% aqueous K$_2$CO$_3$ (120 g.) at 0° and the oil which separated was extracted with CH$_2$Cl$_2$ (2×100 ml.). The CH$_2$Cl$_2$ layer was washed with a little water, brine and then dried to give the crude imidate (14 g.). This was stirred with NH$_4$Cl (3.5 g.) in MeOH (100 ml.) for 24 hours and the solution was evaporated to give a crude sample (14.6 g.) of 4-benzyloxybutanamidine hydrochloride.

To a mixture of 4-benzyloxybutanamidine hydrochloride (14.6 g.) and triethylamine (33 g.) in EtOH (80 ml.) was added 2-chloroacrylonitrile (11.3 g.) and the solution was heated under reflux for 2 hours and then evaporated to dryness. The residue was partitioned between 10% aqueous HOAc (100 ml.) and EtOAc (200 ml.) and the EtOAc was reextracted with 10% v/v aqueous HOAc (2×100 ml.). The combined aqueous layers were basified with concentrated aqueous NaOH and extracted with EtOAc (3×75 ml.) and the EtOAc solution was washed with brine and dried to give 4-amino-2-(3-benzyloxypropyl)pyrimidine (9.8 g.). This amino-derivative was heated under reflux with 2,2,2-trifluoroethylisothiocyanate (10 g.) in acetonitrile (20 ml.) for 23 hours and the mixture evaporated to dryness. The residue was chromatographed on silica gel using CH$_2$Cl$_2$ containing 1% v/v MeOH as eluant to give 2-(3-benzyloxypropyl)-4-[3-(2,2,2-trifluoroethyl)thioureido]-pyrimidine (10 g.).

This thiourea was stirred for 18 hours with yellow mercuric oxide (10 g.) in methanolic ammonia (250 ml.). The mixture was filtered, the filtrate was evaporated to dryness and the residue was extracted with hot CH$_2$Cl$_2$. Evaporation of the CH$_2$Cl$_2$ solution gave 2-(3-benzyloxypropyl)-4-[2-(2,2,2-trifluoroethyl)guanidino]pyrimidine (9.2 g.) which was used without further purification.

EXAMPLE 14

The process of Example 13 was repeated using 2-(4-benzyloxybutyl)-4-[2-(2,2,2-trifluoroethyl)guanidino]-pyrimidine as starting material to give 2-(4-hydroxybutyl)-4-[2-(2,2,2-trifluoroethyl)guanidino]pyrimidine, m.p. 135°–136° (yield 40%).

The starting material may be prepared by repeating the second, third and fourth parts of Example 13, using 5-benzyloxyvaleronitrile in place of 4-benzyloxybutyronitrile.

EXAMPLE 15

A mixture of 2-(2-acetoxyethylthiomethyl)-4-aminopyrimidine (1.5 g.) and 2,2,2-trifluoroethylisothiocyanate (1.7 ml.) in acetonitrile (10 ml.) was heated under reflux for 16 hours. The solvent was evaporated in vacuo and the residue in DMF (10 ml.) was stirred with yellow mercuric oxide (3 g.) at room temperature. Methanolic ammonia solution (6 M; 10 ml.) was added and the mixture stirred for 16 hours. Potassium hydroxide (1 g.) in water (5 ml.) was added and stirring continued for a further 6 hours. The mixture was diluted with water (20 ml.) and EtOAc (100 ml.), the aqueous phase adjusted to pH 9 with dilute aqueous hydrochloric acid and both phases filtered through diatomaceous earth. The organic phase was separated, washed with brine, dried (MgSO$_4$) and evaporated to give a gum which was purified by medium pressure liquid chromatography on silica gel using EtOAc/MeOH mixtures as eluant. There was thus obtained 2-(2-hydroxyethylthiomethyl)-4-[2-(2,2,2-trifluoroethyl)guanidino]pyrimidine (0.3 g.), m.p. 157°–158° after recrystallisation from EtOAc/toluene.

The starting material may be prepared as follows.

To a solution of chloroacetamidine hydrochloride (11 g.) in EtOH (50 ml.) was added triethylamine (24 ml.) and 2-chloroacrylonitrile (6.8 ml.) and the mixture was heated under reflux for 10 minutes. The dark solution was evaporated to dryness in vacuo, the residue dissolved in EtOAc, the solution decolourised with carbon, filtered and the filtrate evaporated. Ether was added and the solution filtered to remove some insoluble material. Evaporation gave 4-amino-2-chloromethylpyrimidine (5 g.), m.p. 125°–128°.

4-Amino-2-chloromethylpyrimidine (2.8 g.) and thiourea (1.6 g.) in EtOH (80 ml.) were heated under reflux for 20 minutes. The mixture was cooled and the precipitated thiouronium salt (4 g.) isolated by filtration. A solution of this salt (4 g.) in aqueous potassium hydroxide solution (2.2 g. KOH in 40 ml.) was stirred at 45° for 1.5 hours under an atmosphere of nitrogen. 2-Bromoethanol was added and the solution stirred for 0.5 hours at 45° then left for 16 hours at 25°. The solution was adjusted to pH 8 with dilute aqueous hydrochloric acid, saturated with sodium chloride and extracted with EtOAc (3×50 ml.). The combined extracts were dried (MgSO$_4$) and evaporated. Crystallisation of the residue from EtOH/EtOAc gave 2-(2-hydroxyethylthiomethyl)-4-aminopyrimidine, m.p. 131°–134°.

A mixture of 2-(2-hydroxyethylthiomethyl)-4-aminopyrimidine (1.5 g.) in HOAc (5 ml.) and acetic anhydride (5 ml.) was stirred at 25° for 16 hours. The solvent was evaporated in vacuo to give 2-(2-acetoxyethylthiomethyl)-4-aminopyrimidine as a gum which was used without further purification.

EXAMPLE 16

The process of Example 15 was repeated, using 2-(2-acetoxyethoxymethyl)-4-aminopyrimidine as starting material, to give 2-(2-hydroxyethoxymethyl)-4-[2-(2,2,2-trifluoroethyl)guanidino]pyrimidine, m.p. 144°–146°.

The starting material may be prepared as follows:

Ethylene glycol (25 ml.) was added dropwise to a stirred suspension of sodium hydride (2 g. of 50% w/w suspension in oil) in dry toluene (25 ml.). When reaction ceased toluene was distilled from the mixture, 4-amino-2-chloromethylpyrimidine (2.8 g.) was added and the mixture stirred for 16 hours. Acetic anhydride (100 ml.) was added in small portions to the mixture with external cooling and the resulting solution stirred at 25° for 2 hours. Excess acetic anhydride was carefully hydrolysed by slow addition of water (150 ml.) and the mixture adjusted to pH 1 with aqueous HCl. The mixture was washed with ether (× 3), the aqueous phase brought to pH 8 by addition of dilute aqueous sodium hydroxide and extracted with EtOAc (3×100 ml.). The combined extracts were washed with brine, dried (MgSO$_4$) and evaporated to give a brown oil from which 2-(2-acetoxyethoxymethyl)-4-aminopyrimidine (1.6 g.) was isolated by medium pressure liquid chromatography on silica gel using EtOAc/MeOH 9:1 v/v as eluant.

EXAMPLE 17

The process of Example 15 was repeated using 2-(3-acetoxypropoxymethyl)-4-aminopyrimidine as starting material to give 2-(3-hydroxypropoxy)-4-[2-(2,2,2-trifluoroethyl)guanidino]pyrimidine m.p. 118°–120°.

The starting material may be prepared by the process described in Example 16, part 2, using propylene glycol in place of ethylene glycol.

EXAMPLE 18

A mixture of 1,3-propanedithiol (1 ml.), sodium methoxide (0.08 g.), 4-[2-(2,2,2-trifluoroethyl)guanidino]-2-methylsulphinylpyrimidine (0.28 g.) and MeOH (10 ml.) was stirred at room temperature for two hours and then evaporated to dryness. The residue was partitioned between N aqueous hydrochloric acid and ether, and the aqueous phase was basified and then extracted with EtOAc. The EtOAc extract was dried and evaporated to dryness. A solution of the residue in acetone was added to a solution of maleic acid in acetone, and the crystalline precipitate collected to give 4-[2-(2,2,2-trifluoroethyl)guanidino]-2-(3-mercaptopropylthio)-pyrimidine hydrogen maleate (0.26 g.), m.p. 153°–155°.

EXAMPLE 19

A mixture of 4-amino-2-(3-hydroxypropylthio)-pyrimidine (0.5 g.), 2,2,2-trifluoroethylisothiocyanate (0.47 g.) and acetonitrile (2 ml.) was heated under reflux for 18 hours and then evaporated to dryness. The residue was dissolved in ethanolic ammonia solution and the solution treated with yellow mercuric oxide (0.7 g.). The mixture was stirred at room temperature for 18 hours and then filtered and the filtrate was evaporated to dryness. The residue was dissolved in a mixture of EtOH (10 ml.) and concentrated aqueous ammonia (10 ml.) and the mixture heated under reflux for four hours with the addition of 7×1 ml. portions of concentrated aqueous ammonia at intervals of 0.5 hours. The mixture was evaporated to dryness and the residue was partitioned between N aqueous hydrochloric acid and EtOAc. The aqueous phase was basified and extracted with EtOAc and the extract was dried and evaporated to dryness. A solution of the residue in acetone was added to a solution of maleic acid in acetone and the precipitate collected and recrystallised from EtOH to give 4-[2-(2,2,2-trifluoroethyl)guanidino]-2-(3-hydroxypropylthio)pyrimidine hydrogen maleate (0.11 g.), m.p. 168°–170°.

The starting material may be prepared as follows:

A mixture of 2-thiocytosine (0.88 g.), sodium hydroxide (0.32 g.), water (5 ml.) and 3-chloropropanol (0.8 g.) was heated at 90° for 1 hour and then cooled. The mixture was extracted with EtOAc and the extract dried and then evaporated to dryness to give 4-amino-2-(3-hydroxypropylthio)pyrimidine (1.5 g.) which was used without further purification.

EXAMPLE 20

The process of Example 19 was repeated using 3-amino-5-(3-hydroxypropylthio)-1,2,4-triazole as starting material to give 3-[2-(2,2,2-trifluoroethyl)-guanidino]-5-(3-hydroxypropylthio)-1,2,4-triazole hydrogen maleate (yield 3%), m.p. 150°–152°.

The starting material may be prepared as follows:

A mixture of 3-amino-5-mercapto-1,2,4-triazole (1.16 g.), 2 N aqueous sodium hydroxide (6 ml.) and 3-chloropropanol (1.1 g.) was heated at 90° for 1 hour and then cooled. The white solid which crystallised was collected to give 3-amino-5-(3-hydroxypropylthio)-1,2,4-triazole (1.15 g.), m.p. 136°–137°.

EXAMPLE 21

A mixture of 4-[2-(2,2,2-trifluoroethyl)guanidino]-2-methylsulphinylpyrimidine (0.28 g.) and 3-aminopropanol (1 ml.) was heated at 90° for 1 hour and then cooled to room temperature. The mixture was partitioned between water and EtOAc, and the EtOAc phase was dried and evaporated to dryness. A solution of the residue in acetone was added to a solution of maleic acid in acetone, and the precipitate was collected and recrystallised from aqueous EtOH to give 4-[2-(2,2,2-trifluoroethyl)guanidino]-2-(3-hydroxypropylamino)pyrimidine bis hydrogen maleate (0.18 g.), m.p. 148°.

EXAMPLE 22

The process of Example 21 was repeated, using N-methyl-2-hydroxyethylamine as starting material, to give 2-(N-methyl-2-hydroxyethylamino)-4-[2-(2,2,2-trifluoroethyl)guanidino]pyrimidine, m.p. 158°–160° (yield 50%).

EXAMPLES 23–30

The process of Example 1 was repeated, using the appropriate starting materials to give the following compounds:

$$R^1NH\diagdown C=N-\diagup\diagdown N\diagdown N-O-R^2 \diagup H_2N$$

| Example | $R^1$ | $-R^2$ |
|---|---|---|
| 23 | $CF_3CH_2$ | $-(CH_2)_2OH$ |
| 24 | $CHF_2CF_2CH_2$ | $-(CH_2)_3OH$ |
| 25 | $CF_3CH_2$ | ⟨cyclohexyl⟩-OH |
| 26 | $CF_3CH_2$ | $-CH_2-CH=CHCH_2OH$ |
| 27 | $CF_3CH_2$ | $-(CH_2)_2CH(CH_3OH$ |
| 28 | $CF_3CH_2$ | $-(CH_2)_2O(CH_2)_2OH$ |
| 29 | $CF_3CH_2$ | $-(CH_2)_4OCH_3$ |
| 30 | $CF_3CH_2$ | $-(CH_2)_3SCH_3$ |

Notes
Example 23: maleate, m.p. 174–176° (yield 73%).
Example 24: maleate, m.p. 173–174° (yield 62%).
Example 25: maleate, cis/trans mixture, m.p. 182–184° (yield 89%).
Example 26: maleate, cis isomer, m.p. 156–158° (yield 26%).
Example 27: n.m.r. in $d_6$DMSO:- 1.1 (d, 3H); 1.75 (m, 2H); 3.75 (m, 1H); 4.35 (d, 2H); 4.4 (m, 2H); 6.15 (s, 2H); 6.65 (d, 1H); 8.4 (d, 1H).
Example 28: maleate, m.p. 163–164° (yield 87%).
Example 29: maleate, m.p. 186–187° (yield 68%).
Example 30: maleate, m.p. 182–183° (yield 49%).

EXAMPLE 31

4-(2-Propylguanidino)-2-methylsulphinylpyrimidine (200 mg.) was added to a solution of sodium hydride (72 mg.) in 1,3-propanediol (2 ml.) and the mixture stirred at ambient temperature for 1 hour. The mixture was diluted with water and extracted with EtOAc (3×10 ml.). The extract was dried ($MgSO_4$) and evaporated to give a gum which crystallised on standing. Recrystallisation from EtOAc gave 4-(2-propylguanidino)-2-(3-hydroxypropoxy)pyrimidine, m.p. 183°–184° (yield 25%).

The starting material may be prepared as follows:

Cyanamide (1.05 g.) was added to potassium t-butoxide (2.8 g.) in DMF (10 ml.) with stirring to produce a fine suspension of potassium cyanamide. To this was added 4-chloro-2-methylthiopyrimidine (4 g.) and the mixture stirred at ambient temperature for 17 hours. The DMF was evaporated in vacuo and the residue suspended in water (20 ml.), the pH adjusted to 11 with dilute aqueous sodium hydroxide and the mixture extracted with EtOAc (2×10 ml.). The aqueous layer was separated, acidified to pH 3 with dilute hydrochloric acid and the precipitate collected, washed with water and dried to give 4-cyanoamino-2-methylthiopyrimidine, m.p. 189–191 (decomp.).

A mixture of 4-cyanoamino-2-methylthiopyrimidine (0.83 g.) and n-propylamine (0.6 ml.) was heated under reflux in acetonitrile (20 ml.) for 1 hour. The solvent was evaporated in vacuo and the residue suspended in dilute aqueous sodium hydroxide. The solid was collected, washed with water and dried to give 4-(2-propylguanidino)-2-methylthiopyrimidine, m.p. 177°–178°.

A solution of 4-(2-propylguanidino)-2-methylthiopyrimidine (1.6 g.) in MeOH (25 ml.) was heated on a steam bath while a solution of sodium metaperiodate (1.6 g.) in water (15 ml.) was added dropwise over 15 minutes. Further sodium metaperiodate in water (10% w/v) was added until analysis by t.l.c. on silica using EtOAc/MeOH 4:1 v/v as eluant showed absence of starting material. The reaction mixture was evaporated in vacuo, and the residue partitioned between methylene chloride and water. The organic phase was worked up to give 4-(2-propylguanidino)-2-methylsulphinylpyrimidine, m.p. 179°–180°.

EXAMPLE 32

The process described in Example 31 was repeated using 4-(2-i-propylguanidino)-2-methylsulphinylpyrimidine as starting material to give 4-(2-i-propylguanidino)-2-(3-hydroxypropoxy)pyrimidine, m.p. 181°–183° (yield 24%).

The starting material may be prepared by repeating the third and fourth parts of Example 31 using i-propylamine in place of n-propylamine.

EXAMPLE 33

To a solution of methyl 4-[2-(2-[2,2,2-trifluoroethyl]guanidino)thiazol-4-yl]butyrate (0.5 g.) in THF (40 ml.) was added lithium aluminium hydride (0.3 g.) in small portions. The resulting mixture was heated under reflux for 2 hours. The mixture was then cooled and a saturated solution of sodium sulphate was added cautiously until the excess hydride had been decomposed. The mixture was filtered and the filtrate evaporated to dryness. The residue in acetone was treated with an excess of maleic acid in acetone to give 4-(4-hydroxybutyl)-2-[2-(2,2,2-trifluoroethyl)guanidino]thiazole hydrogen maleate. The n.m.r. spectrum in d₆DMSO included the following resonances: 1.5 (m, 4H); 2.5 (m+DMSO), 3.4 (t, 2H); 4.2 (q, 2H); 6.2 (s, 2.5H); 6.6 (s, 1H).

The starting material may be prepared as follows:

To 2,2,2-trifluoroethylamidinothiourea (2.1 g.) in hot EtOH (20 ml.) was added a solution of methyl 6-chloro-5-oxohexanoate (2.0 g.) in hot EtOH (20 ml.). The mixture was heated under reflux for 1 hour and then evaporated to dryness. The residue was partitioned between ether (20 ml.) and water (60 ml.). The aqueous layer was separated, basified with sodium bicarbonate and extracted with EtOAc. The organic layer was evaporated to dryness to give a gum which was recrystallised from EtOAc/ether/acetone to give methyl 4-[2-(2-[2,2,2-trifluoroethyl]guanidino)thiazol-4-yl]butyrate which was used without further purification.

EXAMPLE 34

A solution of methyl 3-[2-(2-[2,2,2-trifluoroethyl]guanidino)thiazol-4-yl]cyclopentanecarboxylate hydrogen maleate (0.2 g.) in THF (15 ml.) was added to lithium aluminium hydride (0.18 g.) in THF (15 ml.). The mixture was heated under reflux for 2 hours, cooled and a saturated solution of sodium sulphate was added slowly until the excess hydride had been decomposed. The mixture was filtered and the filtrate evaporated to dryness. The residue in acetone was treated with an excess of maleic acid in acetone to give 0.2 g. of 1-hydroxymethyl-3-[2-(2-[2,2,2-trifluoroethyl]guanidino)thiazol-4-yl]cyclopentane 1.25 hydrogen maleate, m.p. 152°–155° (yield 97%).

The starting material may be prepared as follows:

Cyclopentane-1,3-dicarboxylic acid monomethyl ester (16 g.) was heated under reflux in thionyl chloride (60 ml.) for 1 hour and then the mixture was evaporated to dryness. The acid chloride product was added to excess diazomethane in ether solution. After standing for 18 hours this solution was evaporated to dryness and the residue dissolved in acetone and treated with aqueous hydrochloric acid until evolution of nitrogen had ceased. Addition of water then gave a precipitate of the chloroketone, 3.0 g. Of this material was heated under reflux in EtOH (40 ml.) with 2,2,2-trifluoroethylamidinothiourea (2.8 g.) for 2 hours. The mixture was evaporated to dryness and the residue partitioned between water (40 ml.) and EtOAc (60 ml.). The aqueous layer was basified with sodium bicarbonate and extracted with EtOAc. The EtOAc layer was evaporated to dryness and the residue purified by chromatography on silica gel using chloroform/MeOH/aqueous ammonia (s.g. 0.880) 9:1:0.05 v/v/v as eluant to give methyl 3-[2-(2-[2,2,2-trifluoroethyl]guanidino)thiazol-4-yl]cyclopentanecarboxylate as a gum which was used without further purification.

EXAMPLE 35

The process of Example 3 was repeated using 6-[3-(2,2,2-trifluoroethyl)thioureido]-2-(4-hydroxybutoxy)-pyridine as starting material to give 6-[2-(2,2,2-trifluoroethyl)guanidino]-2-(4-hydroxybutoxy)pyridine maleate, m.p. 161°–163° (yield 55%).

The starting material may be prepared by repeating the second part of Example 3, using butane-1,4-diol in place of propane-1,3-diol.

EXAMPLE 36

Propane-1,3-diol (5 ml.) was added to sodium hydride (50% w/w dispersion in oil; 0.228 g.), previously washed with petroleum ether (b.p. 60°–80°). The mixture was heated on a steam bath until no further effervescence occured. After addition of 2-chloro-6-(2-[2,2,2-trifluoroethyl]guanidino)pyrazine (0.4 g.) the mixture was heated on a steam bath for 18 hours. After cooling, 2 N aqueous hydrochloric acid was added and the mixture extracted with EtOAc. The aqueous phase was basified with 2 N aqueous sodium hydroxide and extracted with EtOAc (2×15 ml.). The combined extracts were dried (MgSO₄) and evaporated. The residue was dissolved in a small volume of EtOAc and excess of a solution of maleic acid in EtOAc was added. The resulting solution was diluted with ether until crystallisation began and the solution was allowed to stand at room temperature, then cooled overnight in the refrigerator to give 6-(2-[2,2,2-trifluoroethyl]guanidino)-2-(3-hydroxypropoxy)pyrazine maleate (0.2 g.), m.p. 148°–152°.

The starting material may be prepared as follows:

2,2,2-Trifluoroethylisothiocyanate (6 ml.) was added to 2-amino-6-chloropyrazine (6 g.) in acetonitrile (50 ml.) and the mixture heated under reflux on the steam bath for 6 hours. On cooling the precipitated solid was recrystallised from toluene to give 2-chloro-6-(3-[2,2,2-trifluoroethyl]thioureido)pyrazine, m.p. 170°–172°.

To a solution of 2-chloro-6-(3-[2,2,2-trifluoroethyl]thioureido)pyrazine (0.7 g.) in alcoholic ammonia (35 ml.) was added yellow mercuric oxide (0.65 g.) and the mixture stirred overnight at room temperature. The mixture was filtered and the filtrate evaporated. The residue was recrystallised from toluene/petroleum ether (b.p. 60°–80°) to give 2-chloro-6-(2-[2,2,2-trifluoroethyl]guanidino)pyrazine (0.5 g.), m.p. 139°–140°.

EXAMPLE 37

A stirred mixture of unpurified 4-[3-(2,2,2-trifluoroethyl)thioureido]-2-(3-hydroxymethylphenyl)-1,2,3-triazole (0.473 g.), yellow mercuric oxide (0.31 g.), DMF (1 ml.) and ammoniacal EtOH (6 M; 10 ml.) was kept at room temperature for 45 minutes. The mixture was filtered and evaporated to leave an oil. A solution of this oil in a small volume of EtOAc was treated with a solution of maleic acid (0.166 g.) in a small volume of acetone to give 0.26 g. of 4-[2-(2,2,2-trifluoroethyl)guanidino]-2-(3-hydroxymethylphenyl)-1,2,3-triazole maleate, m.p. 199°–201°.

The starting material may be prepared as follows:

Nitromethane (61 g.) was added to a warm (45°–50°) solution of NaOH (61 g.) in water (122 ml.) at such a rate that the temperature was maintained. At the end of the addition the temperature was raised to 55° for 10 minutes and then allowed to fall back to 50°. The mixture was chilled and neutralised to pH 7 with concentrated hydrochloric acid at ≦10°. The precipitated product was redissolved by the addition of aqueous NaOH (12.5 N; 40 ml.) to give a solution of the sodium salt of methazonic acid. A solution of NaNO₂ (36.2 g.) in water (300 ml.) was added during approximately 30 minutes to a suspension of 3-aminobenzoic acid (68.6 g.) in concentrated hydrochloric acid (126.3 ml.) and water (200 ml.) at 0°–5°. The mixture was filtered to give a solution of 3-carboxybenzenediazonium chloride.

The solution of the sodium salt of methazonic acid was treated at 10° with a cold (5°) solution of 3-carboxybenzenediazonium chloride. A precipitate formed immediately and was dissolved in aqueous NaOH (33% w/w; 100 ml.) to give a dark red solution. The dark red solution was stirred and treated at 25° with acetic anhydride (100 ml.). During this treatment, aqueous NaOH (33% w/w; 200 ml.) was added to keep the mixture basic. The reaction mixture was acidified with concentrated hydrochloric acid and the precipitated product was isolated by filtration to give 101.2 g. of a light brown solid.

A mixture of 23.5 g. of this light brown solid, MeOH (150 ml.) and concentrated sulphuric acid (0.5 ml.) was heated under reflux for 3 hours. The reaction mixture was neutralised with aqueous NaOH (1 N), concentrated and partitioned between CHCl₃ and brine. The CHCl₃ phase was dried (MgSO₄) and evaporated to give 5.9 g. of a red oil that crystallised slowly. The crystallised red oil was purified by medium pressure liquid chromatography on a silica gel column using EtOAc as eluant to give 5.3 g. of a crystalline solid. The solid was recrystallised twice from isopropanol to give 2.7 g. of methyl 3-(4-nitro-1,2,3-triazol-2-yl)benzoate, m.p. (after further recrystallisation from isopropanol) 104°–106°.

A mixture of methyl 3-(4-nitro-1,2,3-triazol-2-yl)benzoate (1.0 g.), 5% w/w palladium on charcoal (0.5 g.) and HOAc (100 ml.) was stirred under one atmosphere of hydrogen until 300 ml. of hydrogen had been absorbed. The reaction was filtered and evaporated to give 0.91 g. of methyl 3-(4-amino-1,2,3-triazol-2-yl)benzoate, m.p. 132°–134° after recrystallisation from MeOH.

A stirred mixture of methyl 3-(4-amino-1,2,3-triazol-2-yl)benzoate (0.312 g.), lithium aluminium hydride (0.10 g.) and ether (50 ml.) was kept at room temperature for 1 hour. The excess of lithium aluminium hydride was destroyed with aqueous NaOH and the mixture was filtered. The filtrate was evaporated to give unpurified 4-amino-2-(3-hydroxymethylphenyl)-1,2,3-triazole.

A mixture of this sample of unpurified 4-amino-2-(3-hydroxymethylphenyl)-1,2,3-triazole, 2,2,2-trifluoroethylisothiocyanate (0.202 g.) and acetonitrile (5 ml.) was kept at room temperature overnight. The mixture was evaporated to leave a residue of unpurified 4-[3-(2,2,2-trifluoroethyl)thioureido]-2-(3-hydroxymethylphenyl)-1,2,3-triazole which was used without further purification.

EXAMPLE 38

A stirred mixture of 4-[3-(2,2,2-trifluoroethyl)thioureido]-2-(4-hydroxybutyl)-1,2,3-triazole (0.75 g.), yellow mercuric oxide (1.0 g.) and ammoniacal EtOH (6 M; 30 ml.) was kept at room temperature for 3 days. The mixture was filtered and the filtrate was evaporated to give an oil. A solution of a portion of this oil (0.28 g.) in a small volume of EtOAc was treated with a solution of maleic acid (0.116 g.) in a small volume of acetone. The produce was precipitated by the addition of ether, isolated by filtration, and washed with EtOAc and then with ether to give 0.25 g. of 4-[2-(2,2,2-trifluoroethyl)guanidino]-2-(4-hydroxybutyl)-1,2,3-triazole maleate, m.p. 115°–117°.

The starting material may be prepared as follows:

A stirred solution of 4-nitro-1,2,3-triazole (1.9 g.) in dry DMF (15 ml.) was treated with a dispersion of sodium hydride (0.4 g.) in mineral oil (0.4 g.). The mixture was stirred at room temperature for 1 hour and then treated with ethyl 4-bromobutyrate (2.4 ml.). The reaction mixture was stirred overnight at room temperature and then poured into water. The product was extracted into EtOAc, dried (MgSO₄), and evaporated to give an oil. This oil was purified by chromatography on silica gel using EtOAc/petroleum ether (b.p. 60°–80°) 1:1 v/v as eluant to give 1.9 g. of ethyl 4-(4-nitro-1,2,3-triazol-2-yl)butyrate.

A suspension of palladium on charcoal (5% w/w; 0.5 g.) in a solution of ethyl 4-(4-nitro-1,2,3-triazol-2-yl)butyrate (0.95 g.) in HOAc (20 ml.) was stirred under one atmosphere of hydrogen until 370 ml. of hydrogen had been absorbed. The mixture was filtered and evaporated to give 0.85 g. of ethyl 4-(4-amino-1,2,3-triazol-2-yl)butyrate as an oil.

Ethyl 4-(4-amino-1,2,3-triazol-2-yl)butyrate (0.85 g.) was added to a stirred mixture of lithium aluminium hydride (2 g.) and ether (40 ml.). The mixture was stirred at room temperature for 4 hours. The excess of lithium aluminium hydride was destroyed with aqueous NaOH. The mixture was filtered. The filtrate was dried (MgSO$_4$) and evaporated to give 0.525 g. of 4-amino-2-(4-hydroxybutyl)-1,2,3-triazole as an oil.

A mixture of 4-amino-2-(4-hydroxybutyl)-1,2,3-triazole (0.46 g.), 2,2,2-trifluoroethylisothiocyanate (0.41 g.) and acetonitrile (15 ml.) was stirred at room temperature overnight. The mixture was evaporated to give 0.75 g. of 4-[3-(2,2,2-trifluoroethyl)thioureido]-2-(4-hydroxybutyl)-1,2,3-triazole, m.p. 102°–103°.

EXAMPLE 19

A tablet containing 100 mg. of 4-[2-(2,2,2-trifluoroethyl)guanidino]-2-(3-hydroxypropylamino)pyrimidine may be prepared using ingredients in the following proportions:

|     |     | mg./tablet |
| --- | --- | --- |
| (a) | Tablet Core. | |
|     | Active agent | 100 |
|     | Lactose | 68.5 |
|     | Calcium carboxymethylcellulose | 22.5 |
|     | Polyvinylpyrrolidone | 6.0 |
|     | Magnesium stearate | 3.0 |
| (b) | Tablet Coat | |
|     | Hydroxypropylmethylcellulose | 4.5 |
|     | Polyethylene glycol | 0.9 |
|     | Titanium dioxide | 1.35 |

The active agent, lactose and calcium carboxymethylcellulose are mixed. An aqueous solution of polyvinylpyrrolidone is added, and the mass is then mixed until it is suitable for granulation. The mass is then granulated and dried. The magnesium stearate is blended with the dried granules and the resulting mixture is compressed into tablets. The tablets are film-coated using an aqueous or solvent suspension of hydroxypropylmethylcellulose, polyethylene glycol and titanium dioxide.

I claim:

1. A guanidine derivative of the formula I:

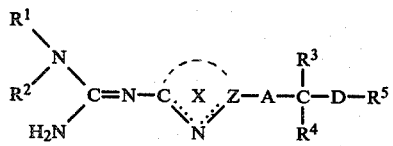

in which $R^1$ and $R^2$, which may be the same or different, are hydrogen or branched or unbranched 1-10C alkyl, 3-8 C cycloalkyl or 4-14C cycloalkylalkyls, each alkyl, cycloalkyl or cycloalkylalkyl being optionally substituted by one or more halogens selected from fluorine, chlorine and bromine, provided that at least one of $R^1$ and $R^2$ is a halogen-substituted alkyl, cycloalkyl or cycloalkylalkyl, and provided that there is no halogen substituent on the carbon of the alkyl, cycloalkyl or cycloalkylalkyl which is directly attached to the nitrogen atom;

ring X is selected from pyrazine, pyridine, pyrimidine and 1,3,5-triazine and which ring may, where possible, carry one or two optional substituents, the optional substituents on ring X being selected from fluorine, chlorine, bromine, 1-6C alkyl, 1-6C alkoxy, 1-6C alkylthio, trifluoromethyl, hydroxy and amino;

—A— is a 1-8C alkylene chain which is optionally substituted by one or two 1-3C alkyls and into which is optionally inserted, as part of the backbone of the chain, an NH or a 1-6C N-alkyl or one or two groups selected from oxygen, sulphur, cis and trans vinylene, ethynylene, phenylene and 5-7C cycloalkylene, provided that no two insertions selected from oxygen, sulphur, NH and N-alkyl are directly attached one to the other and provided that when the optional insertion is NH or N-alkyl, that insertion is directly attached to ring X, or —A— is 5-7C cycloalkylene; $R^3$ is hydrogen, 1-6C alkyl, 3-8C cycloalkyl, 4-12C cycloalkylalkyl, 3-6C alkenyl, 3-6C alkynyl or 2-8C alkoxyalkyl; $R^4$ is hydrogen or 1-6C alkyl; or A—CR$^3$R$^4$ is oxy-1,4-cyclohexylene; D is oxygen or sulphur; $R^5$ is hydrogen, 1-6C alkyl, 1-6C alkanoyl, phenyl, 7-11C phenylalkyl or benzoyl, the phenyl, penylalkyl and benzoyls each being optionally substituted by one or two substituents selected by one or two substituents selected from fluorine, chlorine, bromine, 1-6C alkyl, 1-6C alkoxy, 1-6C alkylthio, cyano, trifluoromethyl, hydroxy and amino:

and the pharmaceutically-acceptable acid-addition salts thereof.

2. A guanidine derivative of the formula I given in claim 1 in which $R^1$ and $R^2$ are selected from the group consisting of hydrogen, 2,2,2-trifluoroethyl, 2,2,2-trichloroethyl, 2-chloro-2,2-difluoroethyl, 2,2-dichloro-2-fluoroethyl, 2-bromo-2,2-difluoroethyl, 2,2-dibromo-2-fluoroethyl, 2-fluoroethyl, 2-chloroethyl, 2,2-difluoroethyl, 2,2-dichloroethyl, 2-chloro-2-fluoroethyl, 2-bromo-2-fluoroethyl, 2,2,3,3-tetrafluoropropyl, 2,2,3,3,3-pentafluoropropyl, 1,1,1,3,3,3-hexafluoroisopropyl, 1,3-dichloro-1,1,3,3-tetrafluoroisopropyl, 1-chloro-1,1,3,3,3-pentafluoroisopropyl, 1,3-difluoroisopropyl, 2,2,3,3,4,4,4-heptafluorobutyl, 2,2,3,3-tetrafluorocyclopropyl, 2-chloro-2,3,3-trifluorocyclopropyl, 2,2-difluorocyclopropyl, 2-chloro-3,3-difluorocyclopropyl, 2,2,3,3,4,4-hexafluorocyclobutyl, 2-chloro-2,3,3,4,4-pentafluorocyclobutyl, (1,2,2,3,3-pentafluorocyclopropyl)methyl, (2-chloro-1,2,3,3-tetrafluorocyclopropyl)methyl, (1,2,2,3,3,4,4-heptafluorocyclobutyl)methyl, (2-chloro-1,2,3,3,4,4-hexafluorocyclobutyl)methyl, methyl, ethyl, propyl, isopropyl, butyl, cyclopropyl, cyclobutyl, cyclopropylmethyl and cyclopropylbutyl, provided that at least one of $R^1$ and $R^2$ is halogen-substituted; in ring X the optional substituents are selected from fluorine, chlorine, bromine, methyl, methoxy, methylthio, trifluoromethyl, hydroxy and amino;

—A— is cyclopentylene, cyclohexylene, methylene, ethylene, trimethylene, tetramethylene, pentamethylene, thiomethylene, thioethylene, thiotrimethylene, thiotetramethylene, thiopentamethylene, oxymethylene, oxyethylene, oxytrimethylene, oxytetramethylene, methylenethiomethylene, methylenethioethylene, methylenethiopropylene, methyleneoxymethylene, methyleenoxyethylene, ethyleneoxyethylene, oxy-2-methylethylene, thiopropylenethiomethylene, oxypropyleneoxy, oxyethyleneoxymethylene, oxyethylenethio, oxypropylenethio, iminomethylene, N-methyliminomethylene, iminopropylene, iminoethylene, vinlyenepropylene, oxymethylene-vinylene, 1,3-phenylene, 1,3-cyclopentylene, methylene-vinylene, 1,3-phenylene, 1,3-cyclopentylene, methylene-1,4-phenylene, ethyleneoxymethylene-1,4-phenylene, oxy-1,3,-phenylenemethylene or thiomethyleneethynylenemethylene; $R^3$ is hydrogen, methyl, cyclohexyl, cyclopropylmethyl, allyl, propargyl or 2-methoxyethyl; $R^4$ is hydrogen or methyl; or A—$CR^3R^4$ is oxy-1,4-cyclohexylene; D is oxygen or sulphur; $R^5$ is hydrogen or methyl, acetyl, phenyl, benzyl or benzoyl, the phenyl, benzyl and benzoyls being optionally substituted by one or two substituents selected from fluorine, chlorine, bromine, methyl, methoxy, methylthio, cyano, trifluoromethyl, hydroxy and amino;

and the pharmaceutically-acceptable acid-addition salts thereof.

3. A guanidine derivative as claimed in claim 2 in which D is oxygen and $R^3$, $R^4$ and $R^5$ are hydrogen.

4. A guanidine derivative as claimed in claim 3 in which $R^2$ is hydrogen and $R^1$ is 2,2,2-trifluoroethyl or 2,2,3,3-tetrafluoropropyl.

5. A guanidine derivative as claimed in claim 4 in which ring X is a pyrimidine ring in which A is linked at the 2-position.

6. A guanidine derivative as claimed in claim 5 in which A is oxyethylene, iminoethylene or trimethylene.

7. A guanidine derivative according to claim 1, said derivative being selected friom the group consisting of 4-[2-(2,2,3,3-tetrafluoropropyl)guanidino]-2-(3-hydroxypropoxy)pyrimidine, and the pharmaceutically-acceptable acid-addition salts thereof.

8. A guanidine derivative selected from the group consisting of 4-[2-(2,2,2-trifluoroethyl)guanidino]-2-(3-hydroxypropoxy)pyrimidine, 2-(4-hydroxybutyl)-4-[2-(2,2,2-trifluoroethyl)guanidino]pyrimidine, 4-[2-(2,2,2-trifluoroethyl)guanidino]-2-(3-hydroxypropylamino)-pyrimidine, 4-[2-(2,2,3,3-tetrafluoropropyl)guanidino]-2-(3-hydroxypropoxy)pyrimidine, and the pharmaceutically-acceptable acid-addition salts thereof.

9. A pharmaceutical composition which comprises a guanidine derivative as claimed in claim 1 in an amount effective to inhibit gastric acid secretion in a warm-blooded animal and in association with a pharmaceutically-acceptabe diluent or carrier.

10. A method of inhibiting gastric acid secretion in a warm-blooded animal which comprises administering to the animal an effective amount of a compound of claim 1.

* * * * *